(12) United States Patent
Sawhney et al.

(10) Patent No.: US 6,564,972 B2
(45) Date of Patent: May 20, 2003

(54) DOUBLE-BARRELED SYRINGE WITH DETACHABLE LOCKING MIXING TIP

(75) Inventors: Ravi K. Sawhney, Calabasas, CA (US); Lance Hussey, Sherman Oaks, CA (US); Robert G. Hayman, Pacific Palisades, CA (US)

(73) Assignee: Dixcus Dental Impressions, Inc., Culver City, CA (US)

( * ) Notice: Subject to any disclaimer, the term of this patent is extended or adjusted under 35 U.S.C. 154(b) by 0 days.

(21) Appl. No.: 10/155,537

(22) Filed: May 23, 2002

(65) Prior Publication Data

US 2002/0145007 A1 Oct. 10, 2002

Related U.S. Application Data

(63) Continuation of application No. 09/581,344, filed as application No. PCT/US99/23604 on Oct. 12, 1999, now Pat. No. 6,394,314.

(51) Int. Cl.[7] .................................................. B67D 5/52
(52) U.S. Cl. ............... 222/137; 222/145.6; 222/153.09; 222/386; 222/459; 239/399
(58) Field of Search ............................. 222/137, 145.6, 222/153.09, 386, 459; 239/399

(56) References Cited

U.S. PATENT DOCUMENTS

| | | |
|---|---|---|
| 3,166,221 A | 1/1965 | Nielsen |
| 3,330,444 A | 7/1967 | Raypholtz |
| 4,538,920 A | 9/1985 | Drake |
| 4,690,306 A | 9/1987 | Staheli |
| 4,753,536 A | 6/1988 | Spehar et al. |
| 4,767,026 A | 8/1988 | Keller et al. |
| 4,776,704 A | 10/1988 | Kopunek et al. |
| 4,974,756 A | 12/1990 | Pearson et al. |
| 4,989,758 A | 2/1991 | Keller |
| 4,995,540 A | 2/1991 | Colin et al. |
| 5,033,650 A | 7/1991 | Colin et al. |
| 5,080,262 A | 1/1992 | Herold et al. |
| 5,236,108 A | 8/1993 | House |
| 5,333,760 A | 8/1994 | Simmen |
| 5,401,169 A | 3/1995 | Fleisher et al. |
| 5,413,253 A | 5/1995 | Simmen |
| 5,443,183 A | 8/1995 | Jacobsen et al. |
| 5,445,614 A | 8/1995 | Haber et al. |
| 5,462,317 A | 10/1995 | Keller |
| 5,482,177 A | 1/1996 | Keller |
| 5,487,606 A | 1/1996 | Keller |
| 5,573,281 A | 11/1996 | Keller |
| 5,609,271 A | 3/1997 | Keller et al. |
| 5,624,260 A | 4/1997 | Wilcox et al. |
| 5,819,988 A * | 10/1998 | Sawhney et al. ........... 222/137 |
| 5,875,928 A | 3/1999 | Muller et al. |
| RE36,235 E | 6/1999 | Keller et al. |
| 5,918,772 A | 7/1999 | Keller et al. |
| 6,065,645 A * | 5/2000 | Sawhney et al. ........... 222/137 |
| 6,119,900 A | 9/2000 | Iwamoto et al. |
| 6,186,363 B1 | 2/2001 | Keller et al. |
| 6,394,314 B1 * | 5/2002 | Sawhney et al. ........... 222/137 |

FOREIGN PATENT DOCUMENTS

| | | |
|---|---|---|
| EP | 0 232 733 B1 | 10/1989 |
| EP | 0 261 466 B1 | 7/1990 |

* cited by examiner

Primary Examiner—Joseph A. Kaufman
(74) Attorney, Agent, or Firm—Christie, Parker & Hale, LLP

(57) ABSTRACT

A double-barreled syringe is provided which includes a mixing tip which is detachable after the tip is locked to the syringe body, so that the tip may be replaced by a locking cap. Locking occurs when a neck extending from the body between two shoulders is inserted into a bore in the tip (or, alternatively, the cap) and the tip is rotated so that two symmetrically opposed tabs attached to the tip are each received within a recess determined by a shoulder and a locking rib attached to the shoulder, and two diametrically opposed detents extending from the neck are each received within a recess in the bore surface.

20 Claims, 7 Drawing Sheets

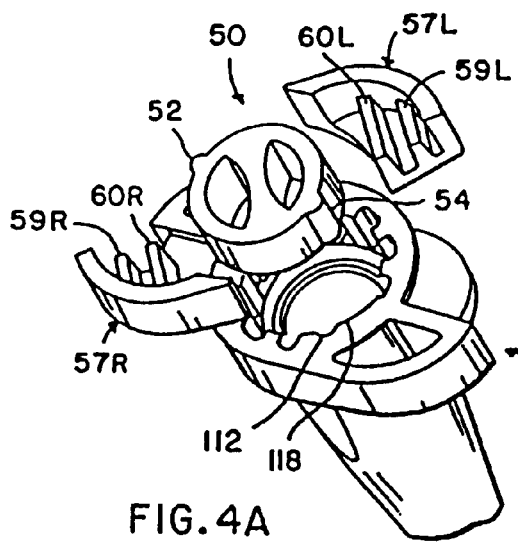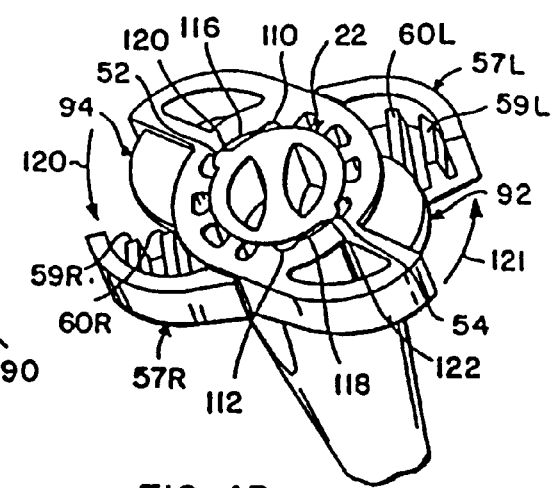
FIG.4A    FIG.4B
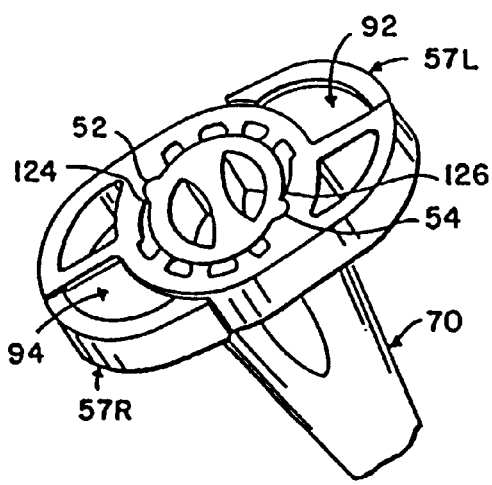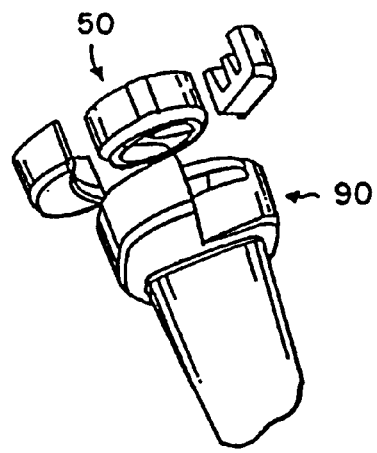
FIG.4C    FIG.5A
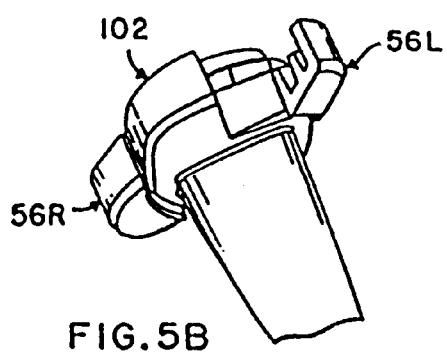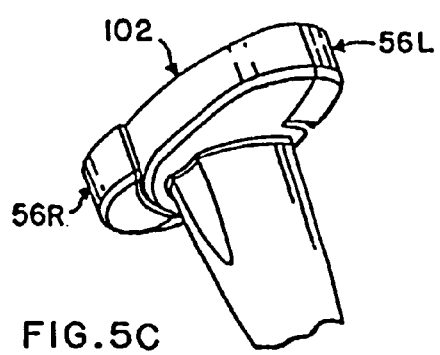
FIG.5B    FIG.5C

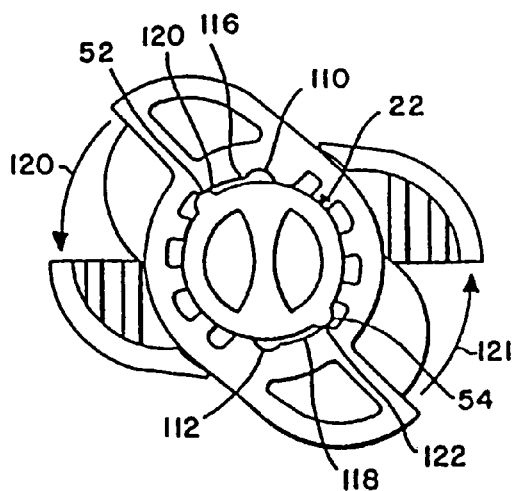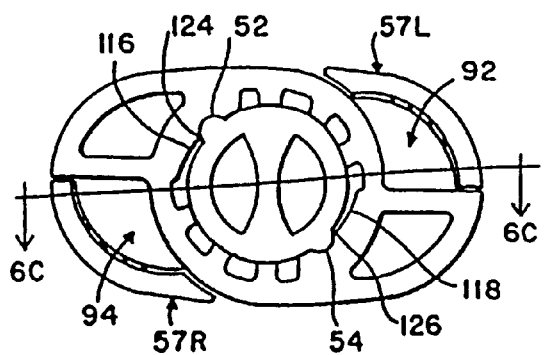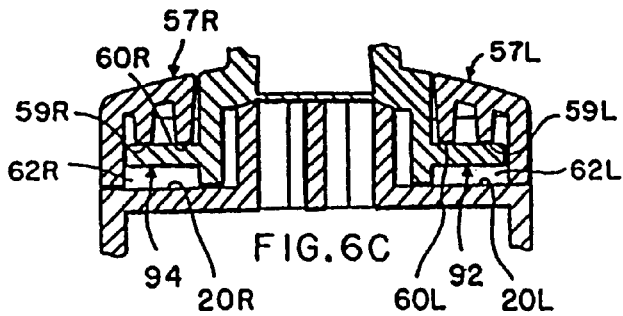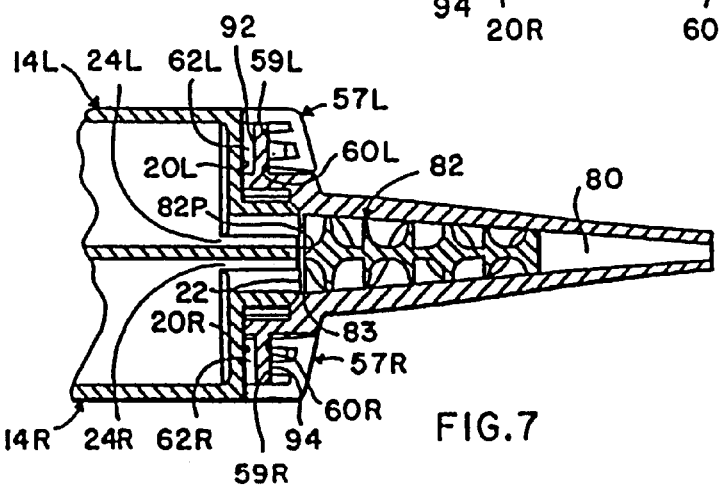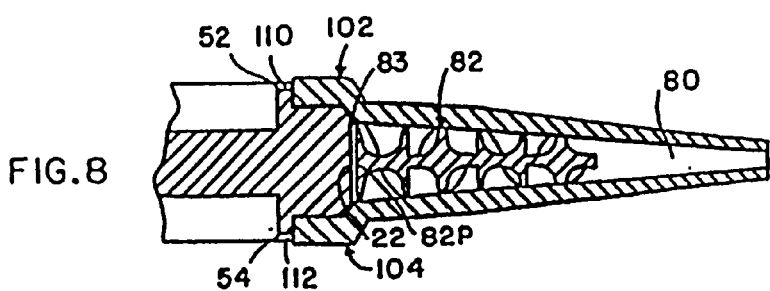

DOUBLE-BARRELED SYRINGE WITH DETACHABLE LOCKING MIXING TIP

CROSS-REFERENCE TO RELATED APPLICATIONS

The present application is a continuation application of Ser. No. 09/581,344, filed Jun. 9, 2000, now U.S. Pat. No. 6,394,314, which claims the benefit of PCT application Ser. No. PCT/US99/23604, filed Oct. 12, 1999; which claims the benefit of Ser. No. 09/170,146, filed Oct. 12, 1998, now U.S. Pat. No. 6,065,645, all having the title "DOUBLE-BARRELED SYRINGE WITH DETACHABLE LOCKING MIXING TIP", their disclosures are hereby incorporated herein by reference.

BACKGROUND OF INVENTION

1. Field of the Invention

The present invention relates to multiple-barreled devices for mixing together and dispensing viscous substances. More particularly, the invention relates to a double-barreled syringe having a double-barreled plunger of unitary construction for dispensing an admixture formed when two gels stored in the barrels are simultaneously discharged into a mixing tip having a five section static mixing element. The tip, which interlocks with the syringe body, is detachable and may be replaced by a locking closure cap to prevent leakage when the syringe is not in use. The locking closure cap preferably has a liner which mitigates undesirable leakage during transport and storage.

2. Description of the Related Art

Devices for mixing and dispensing a viscous fluid having separately stored constituents wherein a mixing portion is detachably connected to a storage portion are known in the art. U.S. Pat. No. 5,413,253 to C. Simmen discloses a static mixer for connection to a cartridge having at least two chambers containing different materials. The mixer is connected to the cartridge by inserting hollow circular make prongs and arcuate positioning keys of a center plug within corresponding female outlets in the cartridge. The plug is rotatably mounted within the collar of a sleeve. The mixer is locked to the cartridge by rotating the collar until opposed tabs on the sleeve engage with locking arms on the dispensing end of the cartridge.

U.S. Pat. No. 4,538,920 to G. E. Drake discloses a double-barreled syringe for mixing and dispensing a two-component material such as a resin and its hardener. Both a mixing tip and a static mixing element located within the tip bore are flexibly rotationally aligned with the syringe body so that the first blade of the mixing element is generally perpendicular to the plane of contiguity between the two component streams exiting a syringe body outlet. The mixing tip is connected to the body by centering the tip inlet over the body outlet while aligning the tip so that it can be pushed between opposed bayonet locking tabs, each having a prong and a stop surface, and then rotating the tip so that opposed ramps on the tip inlet end are wedged between the prongs, and a stop surface proximate to each ramp engages a tab stop surface.

Although either of these devices enables the storage and mixing portions to be connected and then detached multiple times, both are so complex as to be unsuitable for mass production of inexpensive, throwaway dispensers. What is needed is a device which on demand can thoroughly mix two-component viscous materials and dispense a desired amount of the admixture, which will not leak when set aside, and which can be mass produced at relatively little cost.

OBJECTS OF THE INVENTION

Accordingly, it is an object of the present invention to provide a simple, reliable and convenient device which simultaneously dispenses equal amounts of two well mixed viscous materials as an admixture.

Another object of the invention is to provide a device which can be repetitively used to dispense desired amounts of an admixture.

A further object of the invention is to provide a device having a storage portion and a mixing-dispensing portion which repetitively can be easily connected and then detached, wherein the storage portion does not leak during storage and transport thereof.

A still further object of the invention is to provide a device that is inexpensive to manufacture.

Other objects of the invention will become evident when the following description is considered with the accompanying drawing figures. In the figures and description, numerals indicate the various features of the invention, like numerals referring to like features throughout both the drawings and the descriptions.

SUMMARY OF INVENTION

These and other objects are achieved by the present invention which provides a double-barreled syringe wherein one barrel contains a hydrogen peroxide water-based gel formulation used for teeth whitening, and the other contains a gel formulation including compounds that will accelerate the release of oxygen from the first formulation and consequently increase the reaction rate of the teeth whitening process. The syringe dispenses an admixture formed when the two formulations are simultaneously discharged into a mixing tip having a static mixing element. The tip, which is in locking connection with the syringe body, is replaced by a locking closure cap to prevent leakage when the syringe is not in use.

The syringe body includes a double-barrel assembly having juxtaposed first and second barrels having a common length and a generally cylindrical bore of a common diameter. Each barrel is bounded at a discharge end by first and second shoulders, respectively, with each shoulder having a generally planar surface. The surfaces are coplanar and contiguous. A generally cylindrical neck extends from and is symmetrically disposed between the shoulders. The neck includes first and second outlet passages. Each barrel at its opposite (plunger) end closely receives a piston within its bore. An arcuately-shaped finger-grip circumscribes the contiguous plunger ends of the barrels.

The syringe body further includes a double-plunger assembly having juxtaposed first and second plungers of a common length. Each plunger extends at a proximal end in an end-piece rigidly attached to one of the pistons, and is rigidly attached at a distal end to a thumb-rest common to the plungers.

Alternatively, each plunger has a seal formed integrally therewith at a distal end thereof. The seal preferably comprises a flare having a wall thickness which is sufficiently thin as to flexibly conform to the bore within which it is contained and thus seal the plunger upon which it is formed with respect to the bore.

Further, according to the preferred embodiment of the present invention an alignment ring is formed proximate the distal end of each plunger. The alignment ring is formed proximal of the seal. The alignment ring enhances alignment of the seal with respect to the barrel within which the seal is disposed. The alignment ring is coupled comparatively flexibly to the shaft of the plunger and the alignment ring is coupled comparatively rigidly to the seal, so as to allow the combination of the alignment ring and the seal to move together as a unit with respect to the shaft while also causing the alignment ring and the seal to remain comparatively fixed in position with respect to one another. In this manner, the alignment ring and the seal remain aligned with respect to the bore within which they are disposed regardless of bending of the shaft of the plunger which may occur during use.

According to the preferred embodiment of the present invention, the alignment ring is attached to the shaft by a first neck and the seal is attached to the alignment ring by a second neck. The first neck has a smaller diameter than the second neck so as to facilitate movement of the combination of the alignment ring and the seal relative to the shaft, while maintaining desired relative alignment of the alignment ring with respect to the seal. Thus, the combination of the alignment ring and the seal tends to move as a unit with respect to the shaft (which may bend independently of the alignment ring and the seal).

The syringe body further includes a first mating assembly having diametrically opposed first and second detents extending outwardly from the neck, and opposed first and second locking ribs symmetrically disposed with respect to the neck and rigidly attached, respectively, to the first and second shoulders. Each rib has a plurality of generally planar locking faces generally parallel to and at a common predetermined distance from the neighboring shoulder surface.

The syringe further includes a generally conical mixing tip hag an inlet end and a discharge end and a bore therethrough. The bore has a generally cylindrical portion at the inlet end and extends in a conically tapered portion toward the discharge end. The cylindrical bore portion is determined by a circumferential surface adapted to closely receive the body neck. A four section static mixing element is closely received and wedged within the bore tapered portion. The mixing tip has at the inlet end a second mating assembly having opposed generally planar, arcuate first and second locking tabs of a common predetermined thickness slightly less than the distance between the rib locking faces of the first mating assembly and the neighboring shoulder. Each tab has at least one edge beveled at a common predetermined angle. The tabs are symmetrically disposed with respect to the cylindrical bore portion. The bore circumferential surface includes diametrically opposed first and second detent recesses and first and second ramps which are contiguous at a proximal end, respectively, to the recesses.

Alternatively, a five section static mixing element is received and wedged within the bore tapered portion. It is believed that the use of a five section static mixing element will provide approximately 50% better mixing than the four section static mixing element. Those skilled in the art will appreciate that additional sections of the static mixing element will provide further enhanced mixing and may therefore be desirable.

According to the preferred embodiment of the present invention, each section of the static mixing element comprises a single turn screw. Each screw is clocked, i.e., configured so as to be right or left handed, opposite that of each adjacent screw and is oriented, with respect to the leading and trailing edges thereof, at 90% with respect to each adjacent screw. Thus, as the two viscous materials flow from one screw to the next screw, the viscous materials are split into two portions, so as to effect desired mixing thereof The screws are disposed upon a common shaft. The screws taper in size such that the viscous materials flow through successively smaller screws as the viscous materials are dispensed.

The first and second mating assemblies are conjoined when the neck is inserted into the cylindrical bore portion in a relative orientation such that each detent contacts a ramp distal end, thereby determining an engaged configuration. The assemblies interlock when the mixing tip is rotated in a first direction until each detent, traversing the ramp and reaching the ramp proximal end, is received within a recess. Concurrently, each tab is closely received between one of the pluralities of rib locking faces and a shoulder. The mating assemblies are detachable when the mixing tip is rotated in the opposite direction until the neck and cylindrical bore portion are in the engaged configuration.

Optionally, a locking closure cap is utilized in place of the mixing tip so as to better mitigate leakage during shipping. The locking closure cap attaches to the body in the same manner as the mixing tip. Preferably, the locking closure cap comprises a locking closure cap liner formed of a comparatively resilient material which provides an enhanced seal between the locking closure cap and the body. The locking closure cap liner preferably comprises a groove formed therein and configured so as to receive a partition formed within the neck of the body.

A more complete understanding of the present invention and other objects, aspects and advantages thereof will be gained from a consideration of the following description of the preferred embodiment read in conjunction with the accompanying drawings provided herein.

DESCRIPTION OF THE DRAWINGS

FIG. 4A is a combined exploded perspective and partial sectional view of the FIGS. 2 and 3 mating assemblies before engagement;

FIG. 4B is a combined perspective and partial sectional view of the FIGS. 2 and 3 mating assemblies after engagement;

FIG. 4C is a combined perspective and partial sectional view of the FIGS. 2 and 3 mating assemblies after interlocking;

FIG. 5A is a perspective view of the FIGS. 2 and 3 mating assemblies before engagement;

FIG. 5B is a perspective view of the FIGS. 2 and 3 mating assemblies after engagement;

FIG. 5C is a perspective view of the FIGS. 2 and 3 mating assemblies after interlocking;

FIG. 6A is a transverse sectional view of the FIGS. 2 and 3 mating assemblies after engagement;

FIG. 6B is a transverse sectional view of the FIGS. 2 and 3 mating assemblies after interlocking;

FIG. 6C is a cross-sectional view of the FIG. 6B mating assemblies taken along offset line 6C—6C, showing each locking tab disposed within a recess determined by a FIG. 2 shoulder and locking rib;

FIG. 7 is a horizontal cross-sectional view of the FIG. 2 discharge end and FIG. 3 inlet end when the mixing tip is locked to the double-barrel assembly;

FIG. 8 is a cross-sectional view orthogonal to FIG. 7;

DESCRIPTION OF THE PREFERRED EMBODIMENT

Figure 1:
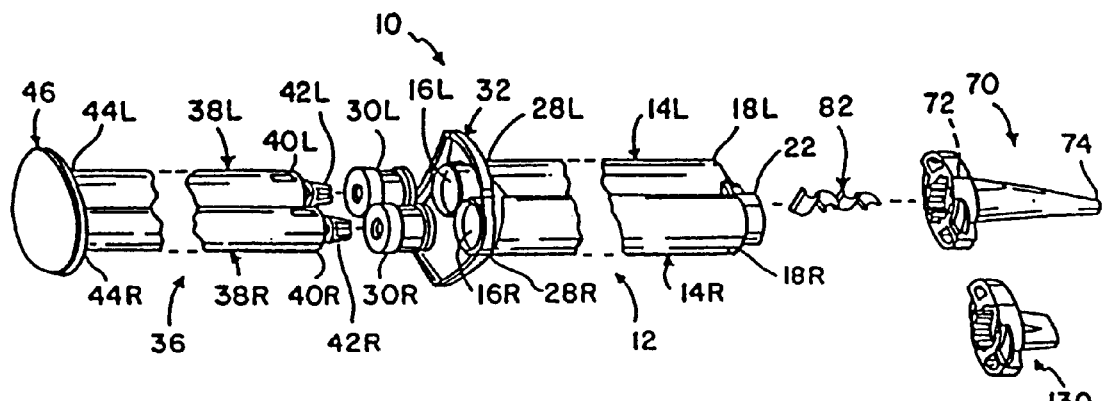
FIG. 1 is an exploded perspective view of a double-barreled syringe according to the invention, including a double-plunger assembly, two pistons, a double-barrel assembly, a static mixing element, a detachable locking mixing tip, and alternatively, a detachable locking cap.

While the present invention is open to various modifications and alternative constructions, the preferred embodiment shown in the drawings will be described herein in detail. It is to be understood, however, there is no intention to limit the invention to the particular form disclosed. On the contrary, it is intended that the invention cover all modifications, equivalences and alternative constructions falling within the spirit and scope of the invention as expressed in the appended claims.

The invention relates to an article of manufacture which is primarily intended for storing and dispensing gels which are components of an admixture and which need to be kept separate until the admixture is formed. However, the invention is not limited to particular types of material to be stored and dispensed, and can be used for storing and dispensing any material that can be placed within a syringe barrel and effectively admixed by a static mixing tip.

Where used herein, the word "attached" means that the two parts referred to (e.g., a locking rib and a shoulder or a plunger end-piece and a piston) are either molded in a single piece, or are glued or force-fitted together. However, other forms of attachment may be suitable, consistent with simplicity of manufacture and reliability of operation. Where used herein, the word "connected" means that the two parts referred to (viz., the two mating assemblies) can be easily separated after being joined together in an interlocking combination.

Figure 2:
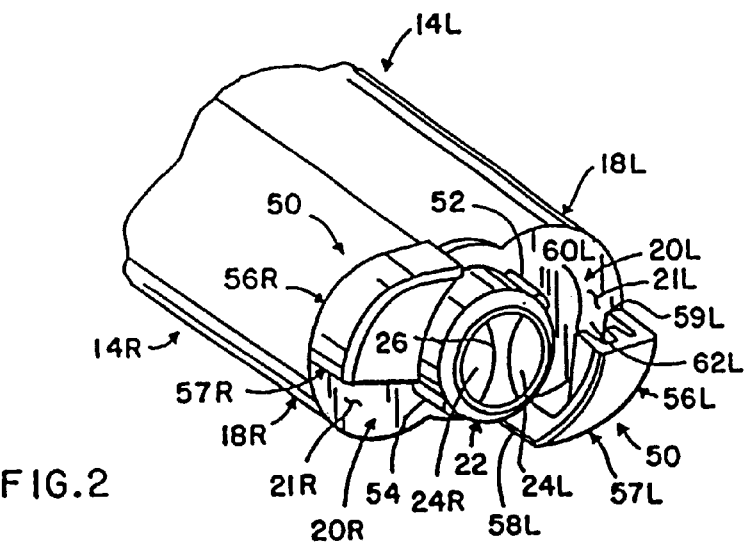
FIG. 2 is a discharge end perspective view of the FIG. 1 double-barrel assembly, including two shoulders, a neck with two outlet passages, and a mating assembly with two diametrically opposed detents and two symmetrically disposed locking ribs for engaging and interlocking with the mixing tip or cap.

Referring to FIGS. 1 and 2, a syringe body 10 includes a double-barrel assembly 12 having juxtaposed first and second generally cylindrical barrels 14L, 14R having a common length and a generally cylindrical bore 16L, 16R, respectively, of a common diameter determining storage compartments 15L (not shown), 15R (not shown). Barrels 14L, 14R are bounded at a first (discharge) end 18L, 18R, respectively, by first and second shoulders 20L, 20R, respectively. The shoulders have generally planar surfaces 21L, 21R, respectively, which are coplanar and contiguous. A generally cylindrical neck 22 extends from and is symmetrically disposed between the shoulders. As shown in FIG. 2, neck 22 includes first and second outlet passages 24L, 24R, divided by a partition 26. As best shown in FIG. 7, passages 24L, 24R are in fluid communication, respectively, with barrels 14L, 14R. Barrels 14L, 14R are open at an opposite (plunger) end 28L, 28R, respectively, which closely receives a piston 30L, 30R, respectively. Barrel ends 28L, 28R are circumscribed by and rigidly attached to an arcuately-shaped finger-grip 32.

The syringe body 10 further includes a double-plunger assembly 36 having juxtaposed generally cylindrical first and second plungers 38L, 38R of a common length. Each plunger extends at an end 40L, 40R proximal to a piston in an end-piece 42L, 42R rigidly attached to the piston 30L, 30R, respectively. The plungers are attached at their distal end 44L, 44R to a disc-shaped thumb-rest 46 so that when the thumb-rest is depressed the plungers move forward in tandem, and the attached pistons move in tandem within the barrels.

Still referring to FIG. 2, syringe body 10 further includes a first mating assembly 50 having diametrically opposed first and second detents 52, 54 extending outwardly from neck 22, and opposed first and second locking ribs 56L, 56R symmetrically disposed with respect to neck 22. Ribs 56L, 56R each have a first (stand-off) portion 57L, 57R, respectively, generally parallel to the shoulders 20L, 20R, respectively, and generally orthogonal to a second (bracket) portion 58L, 58R (not shown), respectively, rigidly attached, respectively, to shoulders 20L, 20R. Rib stand-off portions 57L, 57R each have two generally planar locking faces 59L, 60L, and 59R (not shown), 60R (not shown), respectively, which are generally parallel to and at a common distance from the neighboring shoulder surface 21L, 21R, respectively, thus determining symmetrical recesses 62L, 62R (not shown), respectively. Preferably, double-barrel assembly 12, including neck 22, and mating assembly 50 are fabricated as a unit from a polymerized alkene such as polypropylene by means of an injection molding process.

Figure 3:
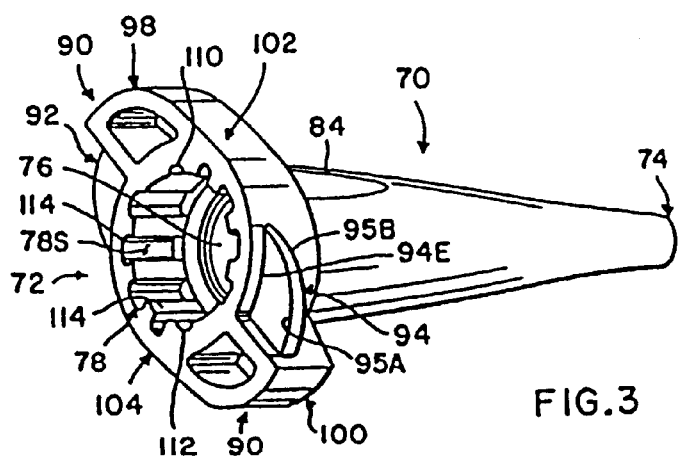
FIG. 3 is an inlet end perspective view of the FIG. 1 mixing tip, including a mating assembly, having two locking tabs, which engages and interlocks with the FIG. 2 mating assembly.

Referring to FIGS. 1 and 3, a generally conical mixing tip 70 includes an inlet end 72 and a discharge end 74 and a bore 76 therethrough. As best shown in FIG. 3, bore 76 has a generally cylindrical portion 78 proximate to inlet end 72 and extends in a conically tapered portion 80 (not shown) toward the discharge end 74. Cylindrical bore portion 78 is determined by a circumferential surface 78S adapted to closely receive the neck 22. As best shown in FIGS. 7 and 8, a static mixing element 82 is closely received and wedged within the tapered bore portion 80. The static mixing element 82 comprises a four section static mixing element. That is, the mixing element 82 is comprised of four separate single turn screws. Mixing element 82 is inserted in a random azimuthal orientation within bore portion 80 and so is not disposed in a predetermined orientation with respect to partition 26 and outlet passages 24L, 24R when mixing tip 70 is attached to double-barrel assembly 12. As further shown in FIGS. 7 and 8, when tip 70 and assembly 12 are attached, proximate end 82P of mixing element 82 and neck 22 are separated by a gap 83. Mixing tip 70 further includes an indented surface portion 84 to facilitate a person holding the tip between the thumb and fingers to rotate the tip.

Still referring to FIG. 3, the inlet end 72 of mixing tip 70 includes a second mating assembly 90 having opposed generally planar arcuately-shaped first and second locking tabs 92, 94 of a common predetermined thickness slightly less than the common width of recesses 62L, 62R. Tabs 92, 94 are symmetrically disposed with respect to cylindrical bore portion 78 and have edges 93A (not shown), 93B (not shown) and 95A, 95B, respectively, which are each beveled at an angle of about 8 degrees. Tabs 92, 94 are rigidly attached, respectively, to structural ribs 98, 100 disposed symmetrically with respect to bore portion 78, and extending in generally oval-shaped collar portions 102, 104, respectively. The two collar portions partially circumscribe inlet end 72 and extend so that tab 92 is rigidly attached at an interior edge 92E (not shown) to collar portion 104, and tab 94 is rigidly attached at an interior edge 94E to collar portion 102. Surface 78S includes diametrically opposed first and second detent recesses 110, 112 and a plurality of corrugations 114. As shown in FIGS. 4A, 4B, 6A and 6B, recesses 110, 112 are each contiguous to first and second ramps 116, 118, respectively, which are generally planar sloping portions of the surface 78S. As shown in FIGS. 4B and 6A, when neck 22 is inserted within bore portion 78, each detent 52, 54 contacts a ramp 116, 118, respectively, at a ramp end 120, 122, respectively, distal to recess 110, 112, respectively. As shown in FIGS. 4C and 6B, when mixing tip 70 is rotated counterclockwise with respect to double-barrel assembly 12, each detent 52, 54 traverses the contacting ramp to the proximal ramp end 124, 126, and is received within the recess. Preferably, mixing tip 70 and associated mating assembly 90 are fabricated as a unit from a polymerized alkene such as polypropylene by means of an injection molding process. As shown in FIG. 1, mixing tip 70 may be replaced by a closure cap 130 having a mating assembly identical to mating assembly 90 so that cap 130 is interchangeable with mixing tip 70.

FIGS. 4A and 5A the proper relative orientation between mating assemblies 50 and 90 so that neck 22 can be inserted into bore portion 78. FIGS. 4B and 6A show the mating assemblies engaged but not yet interlocked. FIG. 5B shows the disposition in the engaged position of collar portion 102 with respect to locking ribs 56L, 56R of mating assembly 50. In FIGS. 4B and 6A, arrows 120, 121 show the (counterclockwise) rotational direction for interlocking. FIGS. 4A and 4B show rib stand-off portions 57L and 57R with respective locking faces 59L, 60L and 59R, 60R. FIGS. 4B and 6A further show the respective disposition of locking tabs 92, 94 of mating assembly 90 and rib stand-off portions 57L, 57R of mating assembly 50 before interlocking. FIGS. 4C and 6B show the respective disposition of locking tabs 92, 94 and rib stand-off portions 57L, 57R after interlocking when tabs 92, 94 have been closely received within recesses 62L, 62R, respectively, and detents 52, 54 received within recesses 110, 112, respectively. Tab insertion and removal are facilitate by beveled edges 93A, 93B of tab 92 and beveled edges 95A, 95B of tab 94. FIG. 5C shows the disposition in the interlocked position of collar portion 102 with respect to locking ribs 56L, 56R. FIGS. 6 and 7 show locking tabs 92, 94 received within recesses 62L 62R, respectively, determined, respectively, by shoulders 20L, 20R and rib stand-off portions 57L, 57R with locking faces 59L, 60L and 59R, 60R. As best shown in FIG. 7, locking tabs 92, 94, when received within recesses 62L, 62R, contact locking faces 59L, 60L and 59R, 60R, respectively. FIG. 8 shows detents 52, 54 in relation, respectively, to recesses 110, 112 and to collar portions 102, 104.

After dispensing a desired amount of admixture, a user typically would detach the mixing tip 70 from the double-barrel assembly 12 by rotating the tip clockwise until detents 52, 54 reach ramp distal ends 120, 122, at which position locking tabs 92, 94 are disengaged from recesses 62L, 62R, and then pulling apart the mixing tip and double-barrel assembly. The corrugation in surface 78S contiguous to each ramp distal end acts as a stop for the detent, thus preventing over-rotation and ensuring that mating assemblies 50 and 90 return to the engaged position. The closure cap 130 may then be connected to the syringe body 10 by using the same engagement and locking procedure as used for the tip.

Preferably, the double-barrel assembly 12 and attached mating assembly 50, double-plunger assembly 36, mixing tip 70 and attached mating assembly 90, and closure cap 130 are fabricated from a polymerized alkene such as polypropylene. Preferably, the length between thumb-rest 46 and discharge end 74 of mixing tip 70 is about 6.75 inches when plungers 38L, 38R are fully retracted. Preferably, the combined width of juxtaposed barrels 14L, 14R is about 0.65 inch.

Figure 9:
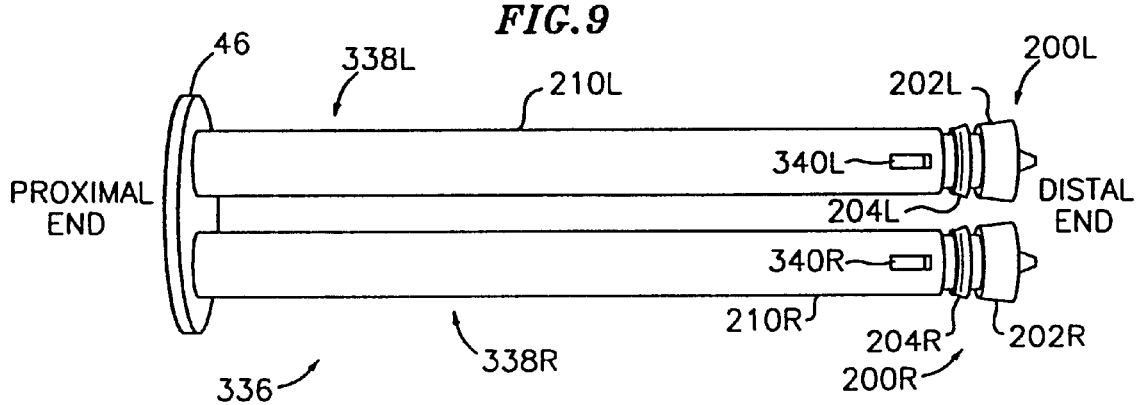
FIG. 9 is a perspective view of a unitary double-barreled plunger having integrally formed seals at the distal ends thereof.
Figure 10:
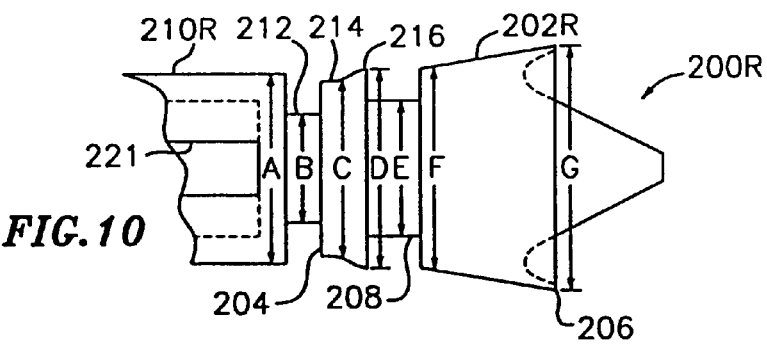
FIG. 10 is an enlarged side view of one of the distal ends of the double-barreled plunger of FIG. 9, showing the seal.
Figure 11:
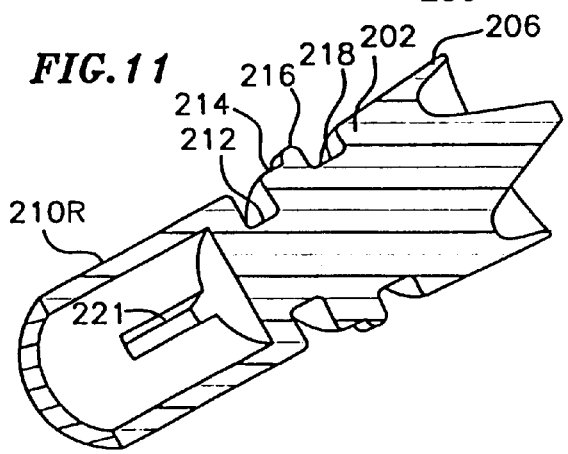
FIG. 11 is a cross sectional perspective view of the distal end of the plunger of FIG. 10.

Referring now to FIGS. 9–11, the plunger alternatively comprises a unitary construction double-barreled plunger 336 having sealing tips 200L and 200R formed integrally with shafts 210L and 210R of the plungers 338L and 338R thereof. In this manner, the need for separate sealing tips, such as those of pistons 30L and 30R of FIG. 1, is eliminated. By eliminating such separate sealing tips, both the materials and assembly costs associated with the plunger assembly 336 are reduced.

With particular reference to FIGS. 10 and 11, the right sealing tip 200R comprises a shaft 210R having a first neck 212 attaching the shaft to 210R to an alignment ring 204 and a second neck 208 attaching the alignment ring 204 to a seal 202R. Although only the distal end of one plunger 338R is shown in FIGS. 10 and 11, it will be appreciated that both plungers 338L and 338R are substantially identical.

The shaft 210R has a diameter, Dimension A, which is substantially greater than a diameter, Dimension B, of the first neck 212. The diameter of the shaft 210R, Dimension A, is somewhat less than the diameter of the cylindrical bore 16R (FIG. 1) within which the shaft 210R is disposed, so as to facilitate easy movement of the shaft 210R within the cylindrical bore 16R. The alignment ring 204 comprises a first portion 214 having a diameter, Dimension C, which is approximately equal to the diameter, Dimension A, of the shaft 210R. The alignment ring 204 also has a second portion 216 which has a diameter, Dimension D, which is greater than the diameter, Dimension C, of the first portion 204 thereof The diameter, Dimension D, of the second portion 216 of the alignment ring 204 is approximately equal to the diameter of the cylindrical bore 16R within which the plunger 338R is slidably disposed, so as to provide a close fit therewith. The second portion 216 preferably defines a radiused or rounded surface where it contacts the cylindrical bore 16R.

Second neck 208 has a diameter, Dimension E, which is less than the diameter, Dimension C, of the first portion 214 of the alignment ring 204 and which is greater than the diameter, Dimension B, of the first neck 212.

The seal 202R has a first portion 220 which has a diameter, Dimension F, which is approximately equal to the diameter, Dimension D, of the second portion 216 of the alignment ring 204 (and which is thus approximately equal to the diameter of the cylindrical bore 16R). The seal 202R also has a second portion 206 which has a diameter, Dimension G, which is substantially greater than the diameter, Dimension F, of the first section 220 of the seal 202R. The second section 206 of the seal 202R is defined by a flare which is comprised of a relatively thin, and consequently comparatively flexible, portion of the seal 202R, and which therefore conforms generally in diameter to the cylindrical bore 16R. In this manner, the second portion 206 of the seal 202R provides a seal between the plunger 38Y and the first bore 16R within which the plunger 338R is disposed.

The alignment ring 204 functions so as to maintain desired alignment of the seal 202R with respect to the cylindrical bore 16R, particularly during use, e.g., dispensing of fluid, of the syringe. During use of the double-barreled syringe, the shaft 210R tends to flex or bow as the thumb rest 46 is pushed so as to force viscous material from the cylindrical bore 16R. The alignment ring 204 mitigates misalignment of the seal 202R and consequent undesirable leakage of viscous material thereby. The alignment ring 204, in combination with the neck 208 and the seal 202R, define a spool-like member which is substantially more resistant to misalignment within the cylindrical bore 16L than is the seal 202R alone.

The first neck 212, which has a substantially smaller diameter, Dimension B, than the diameter, Dimension E, of the second neck 208, permits some desired movement of the shaft 210R of the plunger 338R, with respect to the combination of the alignment ring 204 and the seal 202R (which are rigidly attached to one another) such that bending of the shaft 210R does not effect substantial misalignment of the seal 202R.

The diameter, Dimension C, of the first section 214 of the alignment ring 204 is substantially less than the diameter of the cylindrical bore 16R, and the second section 216 of the alignment ring 204 has a diameter, Dimension D, approximately equal to that of the diameter of the cylindrical bore 16R, so as to provide a desired amount of friction between the alignment ring 204 and the cylindrical bore 16R. The radiused or rounded contact surface of the second section 216 also contributes to providing the desired amount of friction between the alignment ring 204 and the cylindrical bore 16R. According to the preferred embodiment of the present invention, Dimension A is approximately 0.241 inch, Dimension B is approximately 0.129 inch, Dimension C is approximately 0.238 inch, Dimension D is approximately 0.250 inch, Dimension E is approximately 0.165, Dimension F is approximately 0.250 inch and Dimension G. is approximately 0.260 inch. The unitary construction double-barreled plunger 336 is preferably fabricated from a polymerized alkene such as polypropylene.

Figure 12:
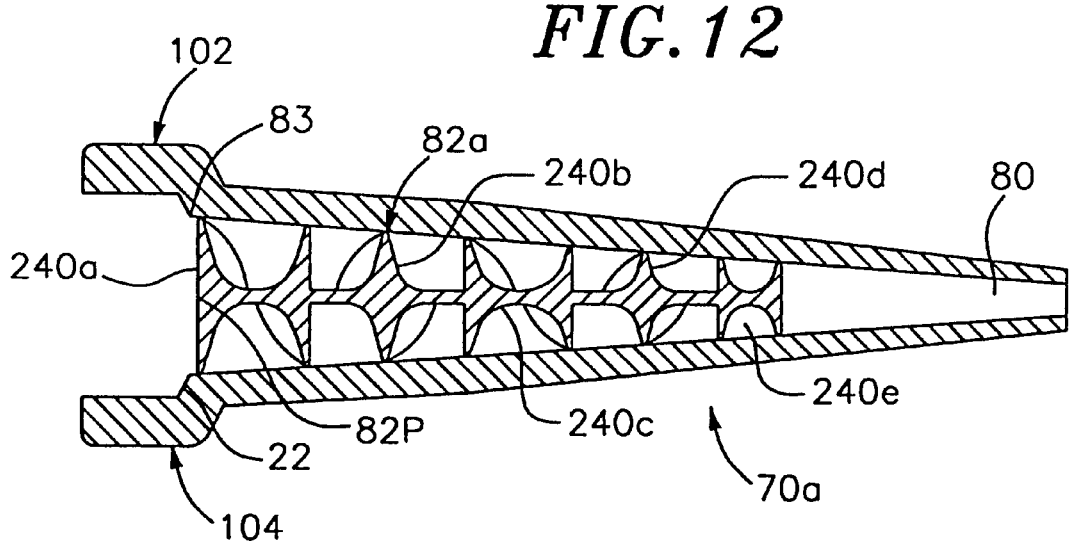
FIG. 12 is a horizontal cross-sectional view of an alternative configuration of the mixing tip, wherein a five element mixer is used instead of the four element mixer of FIGS. 7 and 8.
Figure 13:
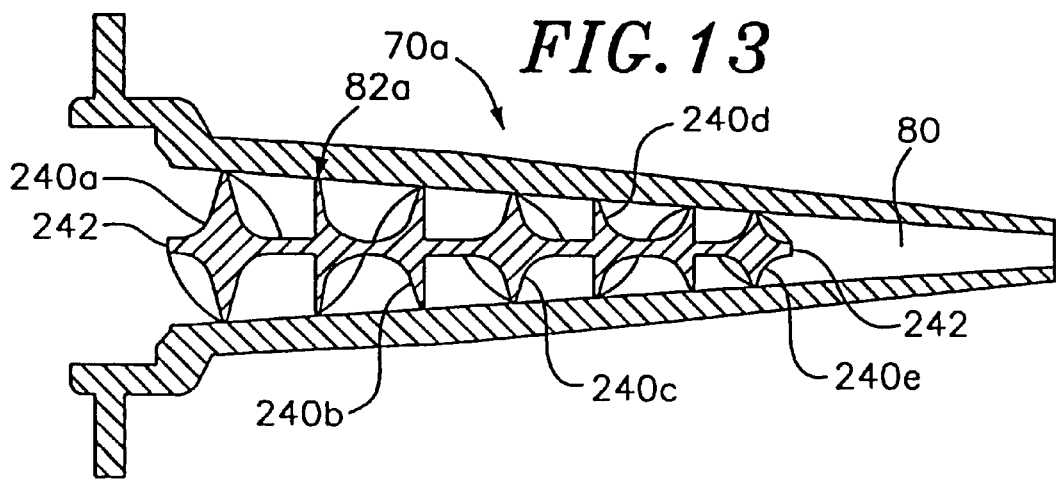
FIG. 13 is a cross-sectional view orthogonal to FIG. 12.
Figure 14:
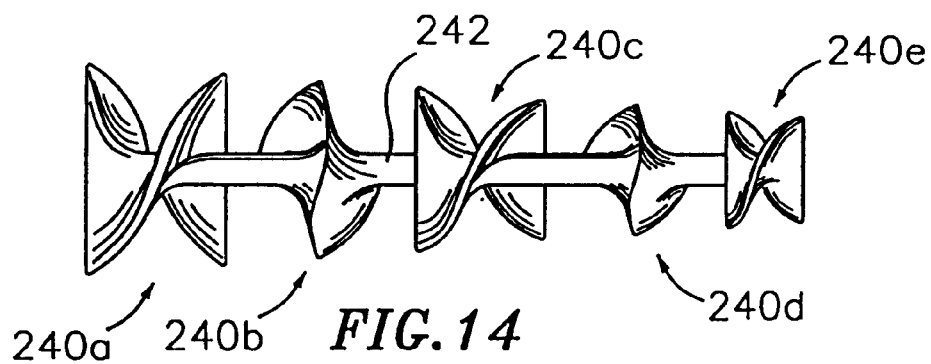
FIG. 14 is an enlarged side view of the five section mixing element of FIGS. 12 and 13.

Referring now to FIGS. 12–14, the mixing tip 70A alternatively comprises a five section static mixing element 82A. The five section static mixing element 82A comprises first 240A, second 240B, third 240C, fourth 240D and fifth 240E sections. Each section 240A–240E of the static mixing element 82A preferably comprises a single turn screw formed upon a common shaft 242 (best shown in FIG. 14) such that each section has a different clock sense, i.e., rotates in a different direction, from each adjacent section. That is, if the screw of a given section 240A–240E is clockwise, then any immediately adjacent section(s) will have a counter clockwise sense. Further, the leading edge of each screw is oriented at approximately 90 degrees with respect to the trailing edge of each preceding screw, such that as fluid flows from one screw to another, the fluid is cut approximately in half, so as to effect desired mixing thereof The five section static mixing element 82A is preferably fabricated from a polymerized alkene such as polypropylene.

Figure 15:
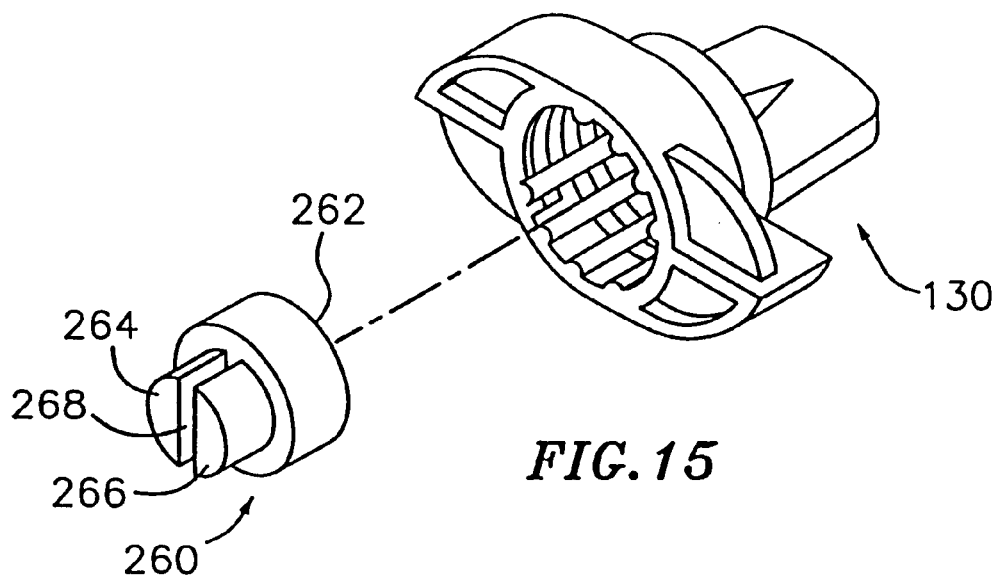
FIG. 15 is a perspective view of a locking closure cap showing the locking closure cap liner thereof exploded therefrom.
Figure 16:
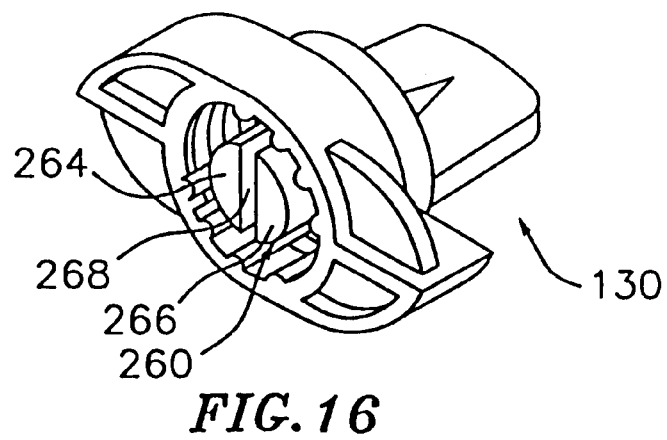
FIG. 16 is an enlarged perspective view of the locking closure cap of FIG. 15, showing the locking closure cap liner installed therein.

Referring now to FIGS. 15 and 16, a locking closure cap 130 preferably comprises a locking closure cap liner 260 for enhancing the seal between the locking closure cap 130 and the neck 22 so as to prevent undesirable leakage of fluids from the first 14L and second 14R cylindrical barrels.

Figure 17:
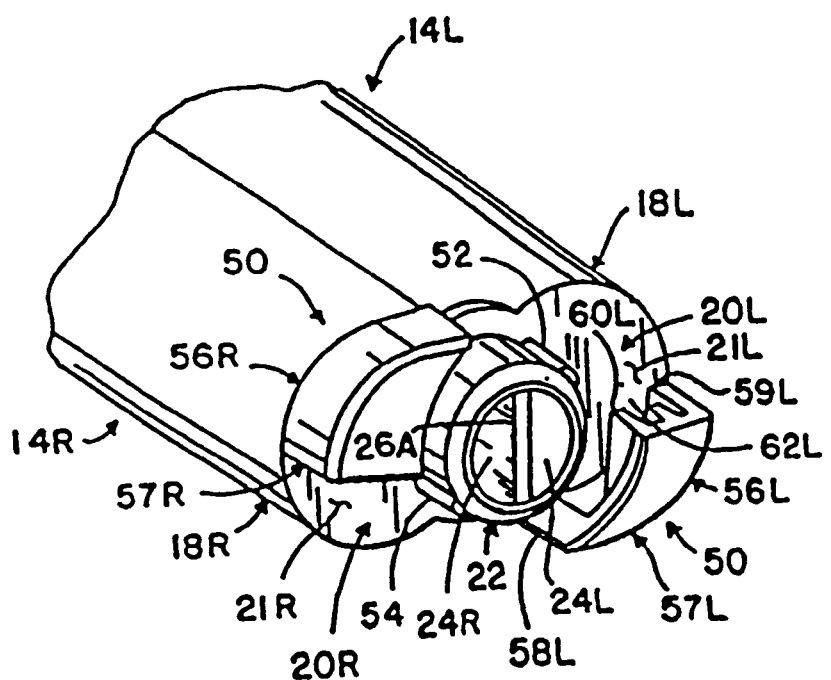
FIG. 17 is a discharge end perspective view of the double-barrel assembly, including two shoulders, a neck with two outlet passages separated by a straight partition, and a mating assembly with two diametrically opposed detents and two symmetrically disposed locking ribs for engaging and interlocking with the mixing tip or cap.

According to the preferred embodiment of the present invention, the locking closure cap liner 260 comprises a base 262 and two outwardly extending protrusions 264 and 266 which define a groove 268 therebetween. The groove 268 is configured so as to receive a generally planar partition 26A of the neck 22, as shown in FIG. 17. The two protrusions fit tightly within the two outlet passages 24L and 24R so as to effect desired sealing thereof The base 262 provides further sealing as it is compressed against the neck 22 by the locking closure cap 130. The base 262 of the locking closure cap 130 is preferably compressed by approximately 0.008 inch when the locking closure cap 130 is attached to the syringe body 10.

The locking closure liner is preferably fabricated from polyolefin elastomer, preferably ENGAGE 8401 (ENGAGE is a federally registered trademark of Dupont Dow Elastomers). The locking closure cap is preferably fabricated form a polymerized alkene, such as polypropylene.

The locking closure cap liner 260 is preferably installed within the locking closure cap by inserting the two outwardly extending protrusions 264 and 266 into the neck 22 such that the partition 26A is received within the locking closure cap liner 260. Then, the locking closure cap 130 is attached to the syringe body 10 in the same manner that the mixing tip 70 is attached thereto. The partition 26A prevents rotation of the locking closure cap liner 260 as the locking closure cap 130 is rotated into the individual position thereof All of the polypropylene components of the present invention are preferably comprised of Polymerland 3320 AP polypropylene.

It is understood that the exemplary double-barreled syringe described herein and shown in the drawings represents only a presently preferred embodiment of the invention. Indeed, various modifications and additions may be made to such embodiment without departing from the spirit and scope of the invention. For example, the unitary construction plunger may alternatively comprise a plurality of alignment rings. Further, various different configurations of the locking closure cap liner are contemplated. Further, various numbers and configurations of the individual sections of the static mixing element are contemplated.

Thus, these and other modifications and additions may be obvious to those skilled in the art and may be implemented to adapt the present invention for use in a variety of different applications.

What is claimed is:
1. A syringe for dispensing two viscous materials as an admixture, comprising:
an integrally molded housing having a first and a second barrel that are symmetrical and fixedly opposed along a center line, the barrels are bounded at a discharge end, have a generally cylindrical neck extending from and symmetrically disposed at the discharge end along the center line, the neck including first and second outlet passages in fluid communication, respectively, with the first and second barrels, an exterior circumferential surface defining the shape of the barrels, and a gripping member disposed at a proximal end of the housing;

a first mating assembly having opposed first and second locking ribs symmetrically disposed with respect to said neck and rigidly attached to the bounded discharge end, the first and second locking ribs having at least a portion aligning with the exterior circumferential surface of the two barrels, and wherein the first mating assembly is configured to receive a mixing tip or a locking closure cap;

wherein the mixing tip has an inlet, an outlet, a generally cylindrical bore defined by a circumferential surface adapted to closely receive said neck, and a second mating assembly having opposed generally planar first and second locking tabs symmetrically disposed with respect to the bore, the two mating assemblies conjoining when the neck is inserted into the mixing tip bore in a relative orientation, and wherein the two mating assemblies interlock when the mixing tip rotates in a first direction and the locking tabs slide under the first and the second locking ribs until a stop is achieved, the two mating assemblies are detachable when the mixing tip is rotated in an opposite direction; and wherein the mixing tip further including a static mixing element having a plurality of intertwined sections disposed within the cylindrical bore for mixing the two viscous materials as the two viscous materials are dispensed from the first and the second barrels.

2. The syringe of claim 1, wherein the intertwined sections comprise a plurality of single turn screws, each screw rotating in a direction opposite that of an adjacent screw and oriented at 90 degrees with respect thereto such that as the two viscous materials flow from one screw to the next screw the viscous materials are split into two portions to effect mixing thereof.

3. The syringe of claim 2, wherein the screws are disposed upon a common shaft.

4. The syringe of claim 2, wherein the screws taper in size such that the viscous materials flow through successively smaller screws as the viscous materials are dispensed.

5. The syringe of claim 1, further comprising a unitary construction double-plunger having juxtaposed first and second plungers of a common length, each plunger being configured to be received by each of the two barrels.

6. The syringe of claim 1, further comprising a unitary construction double-plunger having juxtaposed first and second plungers of a common length, each plunger having an alignment ring formed proximate a distal end thereof and a seal formed distal of the alignment ring, each alignment ring enhancing alignment of a seal with respect to the one of the barrels.

7. The syringe of claim 1, further comprising a unitary construction double-plunger having juxtaposed first and second plungers, each plunger having a shaft, an alignment ring formed at a distal end of the shaft and a seal formed distally of the alignment ring, the alignment ring coupled comparatively flexibly to the shaft of the plunger and the alignment ring coupled comparatively rigidly to the seal.

8. The syringe of claim 1, further comprising a unitary construction double-plunger having juxtaposed first and second plungers, each plunger having a shaft, an alignment ring formed at a distal end of the shaft and a seal formed distally of the alignment ring, the alignment ring attached to the shaft by a first neck and the seal attached to the alignment ring by a second neck, the first neck having a smaller diameter than the second neck to facilitate movement of the alignment ring and the seal relative to the shaft.

9. The syringe of claim 1, further comprising a locking closure cap having a generally cylindrical bore sized to receive said neck, a second mating assembly having opposed generally planar first and second locking tabs symmetrically disposed with respect to said bore, said surface having opposed first and second detent recesses and first and second ramps contiguous at a proximal end, respectively, to said recesses, the mating assemblies conjoining when the neck is inserted into the bore in a relative orientation such that each detent contacts a ramp distal end, thereby determining an engaged configuration, the mating assemblies interlocking when the locking closure cap is rotated in a first direction until each detent, traversing the ramp and reaching the ramp proximal end, is received within a recess, and each tab is closely received between one of said pluralities of rib locking faces and a shoulder, the mating assemblies detachable when the locking closure cap is rotated in the opposite direction until the neck and bore are in said engaged configuration, and a locking closure cap liner comprised of a resilient polymer material disposed within the locking closure cap and configured to engage and seal the neck to mitigate leakage of the two viscous materials from the first and second barrels.

10. The syringe of claim 9, wherein the neck comprises a partition and the locking closure cap liner comprises a groove configured to receive the partition.

11. A syringe for mixing and administering a first and a second content, the syringe comprising:

an integrally molded body portion with two symmetrical barrels having external circumferential surfaces contiguously attached along a center contact line, each barrel having distal and proximal ends; the distal end of each barrel is closed and has an attached locking rib for gripping a mixer, the locking ribs each comprising a first portion which aligns with the external circumferential surface of the corresponding barrel and a second portion which is generally perpendicular to the first portion and which has a face, said proximal end of the barrels includes a gripping member for improved gripping and an inlet for receiving a plunger;

an outlet neck at the closed distal end symmetrically disposed along the center contact line and equally spaced between the locking ribs; wherein said outlet neck is in fluid communication with the two barrels;

wherein the mixer includes an inlet, an outlet, and a bore defined by a circumferential surface adapted to closely receive the outlet neck; the mixer further including a mating assembly which comprises a pair of abutting wall members and a pair of locking tabs, wherein the abutting wall members are configured to abut against the face on the second portion of each of the locking ribs for stopping a relative orientation between the mixer and the outlet neck, and wherein the locking tabs are configured to frictionally engage an underside of the second portion of the locking rib; and wherein the mixer further includes a series of intertwined screws in frictional engagement with the bore.

12. The syringe of claim 11, wherein the static mixing element comprises a plurality of single turn screws, each screw rotating in a direction opposite that of an adjacent screw and oriented at 90 degrees with respect thereto, such that as the two viscous materials flow from one screw to the next screw the viscous materials are split into two portions to effect mixing thereof.

13. The syringe of claim 12, wherein the screws are disposed upon a common shaft.

14. The syringe of claim 12, wherein the screws taper in size such that the viscous materials flow through successively smaller screws as the viscous materials are dispensed.

15. The syringe of claim 11, further comprising a unitary construction double-plunger having juxtaposed first and second plungers of a common length, each plunger being configured to be received by each of the two barrels.

16. A syringe for dispensing two viscous materials as an admixture, comprising:

an integrally molded housing having juxtaposed first and second generally cylindrical barrels having a generally cylindrical bore, the barrels are bounded at a discharge end, have a center line, a generally cylindrical neck extending from and symmetrically disposed at the discharge end along the center line, the neck including first and second outlet passages in fluid communication, respectively, with the first and second barrels, an exterior circumferential surface defining the shape of the barrels, and a gripping member disposed at a proximal end of the housing;

a first mating assembly having opposed first and second locking ribs symmetrically disposed with respect to said neck and rigidly attached to the bounded discharge end, the first and second locking ribs having at least a portion aligning with the exterior circumferential surface of the two barrels, and wherein the first mating assembly is configured to receive a mixing tip or a locking closure cap;

a unitary construction double-plunger having juxtaposed first and second plungers, the first and second plungers are received within the generally cylindrical bores and move from a proximal position to a distal position within the first and second generally cylindrical barrels to dispense the two viscous materials;

wherein the mixing tip has an inlet, an outlet, a generally cylindrical bore defined by a circumferential surface adapted to closely receive said neck, and a second mating assembly having opposed generally planar first and second locking tabs symmetrically disposed with respect to the bore, the two mating assemblies conjoining when the neck is inserted into the mixing tip bore in a relative orientation, and wherein the two mating assemblies interlock when the mixing tip rotates in a first direction and the locking tabs slide under the first and the second locking ribs, the two mating assemblies are detachable when the mixing tip is rotated in an opposite direction; and wherein the mixing tip further including a static mixing element having a plurality of intertwined sections disposed within the cylindrical bore for mixing the two viscous materials as the two viscous materials are dispensed from the first and the second barrels.

17. The syringe of claim 16, wherein the first and second plungers are integrally connected to a push flange at their respective proximal ends.

18. The syringe of claim 16, wherein the screws are disposed upon a common shaft.

19. The syringe of claim 16, further comprising a seal integrally formed at a distal end of each of the first and second syringes for substantially pushing all the viscous materials out of the mixing tip.

20. The syringe of claim 16, wherein the mixing tip includes a taper in between the inlet and the outlet.

* * * * *

Disclaimer

6,564,972 — Ravi K. Sawhney, Calabasa, CA (US); Lance Hussey, Sherman Oaks, CA (US); Robert G. Hayman, Pacific Palisades, CA (US). DOUBLE-BARRELED SYRINGE WITH DETACHABLE LOCKING MIXING TIP. Patent dated May 20, 2003. Disclaimer filed Feb. 25, 2005, by the assignee, Discus Dental Impressions, Inc.

The term of this patent, subsequent to the term of patent number 5,819,988, has been disclaimed.

*(Official Gazette, October 11, 2005)*

UNITED STATES PATENT AND TRADEMARK OFFICE
CERTIFICATE OF CORRECTION

PATENT NO.       : 6,564,972 B2
APPLICATION NO.  : 10/155537
DATED            : May 20, 2003
INVENTOR(S)      : Ravi K. Sawhney et al.

It is certified that error appears in the above-identified patent and that said Letters Patent is hereby corrected as shown below:

On the Title Page

Item (73) Assignee     "Dixcus Dental Impressions, Inc." should be
                       --Discus Dental Impressions, Inc.--

Signed and Sealed this

Twenty-eighth Day of November, 2006

JON W. DUDAS
*Director of the United States Patent and Trademark Office*